(12) United States Patent
Phillips et al.

(10) Patent No.: US 6,890,911 B1
(45) Date of Patent: May 10, 2005

(54) METHOD FOR THE TREATMENT OF INFLAMMATION

(75) Inventors: Nigel C. Phillips, Pointe-Claire (CA); Mario C. Filion, Laval (CA)

(73) Assignee: Bioniche Life Sciences, Inc., Belleville (CA)

( * ) Notice: Subject to any disclaimer, the term of this patent is extended or adjusted under 35 U.S.C. 154(b) by 0 days.

(21) Appl. No.: 09/857,333

(22) PCT Filed: Dec. 3, 1999

(86) PCT No.: PCT/CA99/01156

§ 371 (c)(1),
(2), (4) Date: Sep. 17, 2001

(87) PCT Pub. No.: WO00/33879

PCT Pub. Date: Jun. 15, 2000

Related U.S. Application Data

(60) Provisional application No. 60/110,943, filed on Dec. 4, 1998.

(51) Int. Cl.[7] .............................................. A61K 48/00
(52) U.S. Cl. ..................... 514/44; 424/93.1; 435/243; 435/253.1
(58) Field of Search ........................ 514/44; 424/93.4, 424/93; 435/243, 253.1

(56) References Cited

U.S. PATENT DOCUMENTS

| | | | |
|---|---|---|---|
| 5,759,554 A | * | 6/1998 | Alkemade et al. ........ 424/282.1 |
| 6,326,357 B1 | * | 12/2001 | Phillips et al. ................. 514/44 |

FOREIGN PATENT DOCUMENTS

| | | |
|---|---|---|
| WO | WO 99 07383 A2 | 2/1999 |

OTHER PUBLICATIONS

Heller A. et al. Lipid mediators in inflammatory disorders. Drugs 1998; vol. 55, No. 4, pp. 487–496.*
E Beltan et al., Microbial Pathogenesis, "Secretion of cytokines by human macrophages upon infection by pathogenic and non–pathogenic mycogbacteria," 2000, 28:313–318.*
Bermudez et al.,Infection and Immunity,"Infection with *Mycobacterium avium* Induces Production of Interleukin–10(IL–10),and Administration of Anti–IL–10 Antibody is Associated with Enhanced Resistance to Infection in Mice,"Jul. 1993,vol. 61, No. 7, p3093–3097.*
CAN Moura et al., Immunology, "Lipids from *Mycobacterium leprae* cell wall suppress T–cell activation in vivo and in vitro," 1997, 92, pp. 429–436.*
ACN Moura et al.,Immunology,"Lipids from *Mycobacterium liprae* cell wall suppress T–cell activation in vivo and in vitro," 1997, 92, pp. 429–436.*
MC Filion et al., *Mycobacterium phlei* cell wall complex, a new anti–tumoral agent, induces IL–12 synthesis by monocyte/macrophages via associated DNA, Nov. 1997, Abstract.*
MC Filion et al., J.Pharm. Pharmacol, "Mycobacterial cell wall–DNA complex induces apoptosis in cancer cells," 1998, 50, pp. 39.*
LE Bermudez et at., Infection and Immunity, "Infection with *Mycobacteruim avium* Induces Production of Interleukin–10 . . . Antibody is Associated with Enhanced Resistance to Infection in Mice,"Jul. 1993, pp. 3093–3097.*
Database Biosis Online, Biosciences Information Service, Philadelphia, PA, US Filion, M.C., et al., "Mycobacterial cell wall–DNA complex induces apoptosis in cancer cells", (Sep. 1998), XP002133100, Journ. of Pharmacy and Pharmacology, 135th Meeting of the British Pharmaceutical Conference Eastbourne, England, UK Sep. 8–11, 1998, vol. 50, p. 39.
Database Biosis Online, Biosciences Information Service, Philadelphia, PA, US Filion, M.C., et al., "*Mycobacterium phlei* cell wall complex, a new anti–tumoral agent, induces IL–12 synthesis by monocyte/macrophages via associated DNA", (Nov. 15, 1997), XP002133101, Suppl. 1 Part 2, Thirty–Ninth Annual Meeting of the American Society of Hematology San Diego, California, USA Dec. 5–9, 1997, The American Society of Hematology, vol. 90, p. 58B.

* cited by examiner

*Primary Examiner*—Dave T. Nguyen
*Assistant Examiner*—Jon Eric Angell
(74) *Attorney, Agent, or Firm*—Kilpatrick Stockton, LLP

(57) ABSTRACT

The present invention relates to a mycobacterial deoxyribonucleic acid (B-DNA) preserved and complexed on the mycobacterial cell wall (BCC) and a pharmaceutically acceptable carrier, wherein the BCC is effective in treating an inflammation in an animal having an inflammation. More particularly, the present invention relates to a *Mycobacterium phlei* deoxyribonucleic acid (M-DNA) preserved and complexed on *Mycobacterium phlei* cell wall (MCC) and a pharmaceutically acceptable carrier, wherein the MCC is effective in treating an inflammation in an animal having an inflammation.

21 Claims, 4 Drawing Sheets

METHOD FOR THE TREATMENT OF INFLAMMATION

CROSS REFERENCE TO RELATED APPLICATIONS

This application claims priority to PCT/CA99/01156 filed Dec. 3, 1999 which claims priority to U.S. Provisional Application Ser. No. 60/110,943 filed Dec. 4, 1998.

FIELD OF INVENTION

The present invention relates to a mycobacterial deoxyribonucleic acid (B-DNA) preserved and complexed on a mycobacterial cell wall (BCC), wherein the BCC is effective for treating an inflammation in an animal. More particularly, the present invention relates to Mycobacterium phlei (M. phlei) deoxyribonucleic acid (M-DNA) preserved and complexed on M. phlei cell wall (MCC), wherein the MCC is effective for treating an inflammation in an animal.

BACKGROUND OF THE INVENTION

Inflammation is a complex process initiated by tissue damage. Although inflammation has evolved as a protective response against injury and infection, in certain cases such as, but not limited to, immune-mediated inflammation, osteoarthritis, rheumatoid arthritis, glomerulonephritis, cystitis and colitis inflammation itself is the problem. In these cases, the inflammatory response continues and can be only temporarily modified by the administration of anti-inflammatory agents such as aspirin, nonsteroidal anti-inflammatory drugs and cortisone. These drugs act on the metabolic pathways involved in the elaboration and activation of the pharmacological mediators of inflammation. However, these anti-inflammatory agents have numerous undesirable side effects, and cannot be tolerated by certain individuals.

Therefore, there is a continuing need for novel therapeutic agents that reduce inflammation without having deleterious side effects. Moreover, such therapeutic agents should be simple and relatively inexpensive to prepare, their activity should be reproducible among preparations, their activity should remain stable over time, and their anti-inflammatory effects should be achievable with dose regimens that are associated with minimal toxicity.

SUMMARY OF THE INVENTION

The present invention satisfies the above need by providing a mycobacterial deoxyribonucleic acid (B-DNA) preserved and complexed on a mycobacterial call wall (BCC), wherein the BCC is effective in treating an inflammation in an animal having an inflammation. More particularly, the present invention provides a Mycobacterium phlei (M. phlei) deoxyribonucleic acid (M-DNA) preserved and complexed on M. phlei cell wall (MCC), wherein the MCC is effective in treating an inflammation in an animal having an inflammation.

MCC is simple and relatively inexpensive to prepare, its activity is reproducible among preparations, it remains therapeutically stable over time, and it is effective at dose regimens that are associated with minimal side-effects even upon repeated administration.

To prepare MCC, M. phlei are grown in liquid medium and harvested. The M. phlei are disrupted, and the solid components of the disrupted M. phlei are collected by centrifugal sedimentation. The solid components are deproteinized, delipidated, and washed. DNase-free reagents are used to minimize M-DNA degradation during preparation.

A composition comprising MCC and a pharmaceutically acceptable carrier is administered in an amount effective to prevent, reduce and eliminate an inflammation in an animal, including a human. The unexpected and surprising ability of MCC to reduce inflammation, while itself having minimal side-effects, addresses a long felt unfulfilled need in the medical arts and provides an important benefit for animals, including humans.

Accordingly it is an object of the present invention to provide a composition and method effective to treat an inflammation in an animal having an inflammation.

Another object of the present invention is to provide a composition and method effective to reduce an inflammation in an animal having an inflammation.

Another object of the present invention is to provide a composition and method effective to prevent an inflammation in an animal.

Another object of the present invention is to provide a composition and method effective to eliminate an inflammation in an animal having an inflammation.

Another object of the present invention is to provide a composition and method effective to stimulate IL-10 synthesis in an animal.

Another object of the present invention is to provide a composition and method effective to reduce immune-mediated inflammation in an animal having an immune-mediated inflammation.

Another object of the present invention is to provide a composition and method effective to reduce the inflammation of osteoarthritis in an animal having osteoarthritis.

Another object of the present invention is to provide a composition and method effective to reduce the inflammation of rheumatoid arthritis in an animal having rheumatoid arthritis.

Another object of the present invention is to provide a composition and method effective to reduce the inflammation of glomerulonephritis in an animal having glomerulonephritis.

Another object of the present invention is to provide a composition and method effective to reduce the inflammation of colitis in an animal having colitis.

Another object of the present invention is to provide a composition and method effective to reduce the inflammation of cystitis in an animal having cystitis.

Another object of the present invention is to provide a composition that can be prepared in large amounts.

Another object of the present invention is to provide a composition that is relatively inexpensive to prepare.

Another object of the present invention is to provide a composition that remains stable over time.

Another object of the present invention is to provide a composition that maintains its effectiveness over time.

These and other objects, features and advantages of the present invention will become apparent after a review of the following detailed description of the disclosed embodiment and the appended claims.

DETAILED DESCRIPTION OF THE INVENTION

Figure 1:
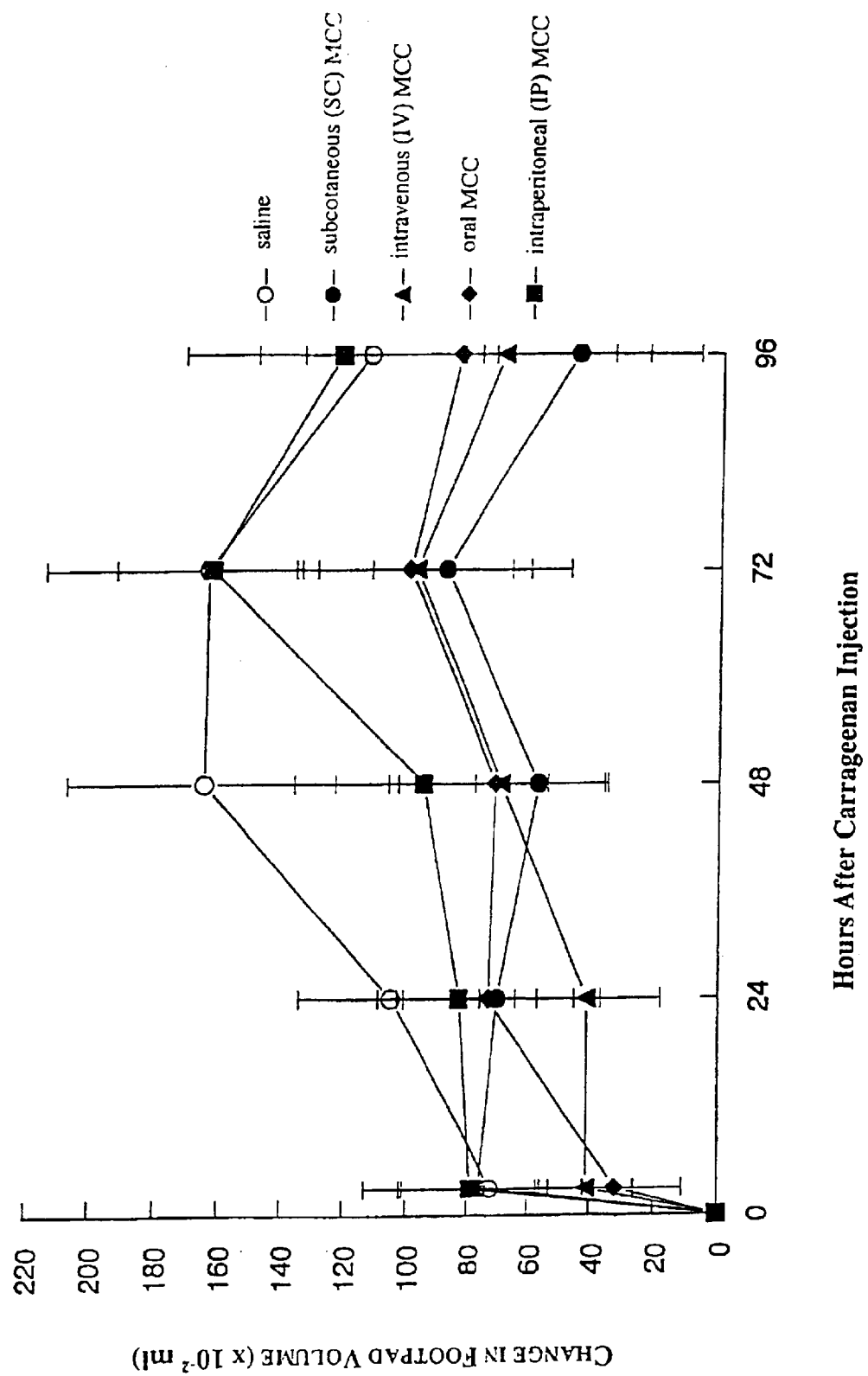
FIG. 1. Effect of intravenous, intraperitoneal, oral and subcutaneous MCC on mouse foot pad volumes at 0, 24, 48, 72 and 96 h after carrageenan injection. Results are the mean ±SD (vertical line) for 8 mice per group.

The present invention comprises a mycobacterial DNA (B-DNA) preserved and complexed on a mycobacterial cell wall (BCC), wherein the BCC is effective in treating an inflammation in an animal having an inflammation. More particularly, the present invention comprises *M. phlei* DNA (M-DNA) preserved and complexed on *M. phlei* cell wall (MCC), wherein the MCC is effective in treating an inflammation in an animal having an inflammation. The present invention further comprises a method for preventing an inflammation in an animal and for eliminating an inflammation in an animal having an inflammation.

As used herein, "treat" relates to a reduction in the volume, pain or spread of an inflammation.
Methods to increase the anti-inflammatory activity of MCC include, but are not limited to, chemically supplementing or biotechnologically amplifying stimulatory sequences or conformations of the M-DNA preserved and complexed on the *M. phlei* cell wall (MCC) and complexing the MCC to natural or synthetic carriers.

MCC is administered in a pharmaceutically acceptable carrier including, but not limited to, a liquid carrier and a solid carrier. Liquid carriers are aqueous carriers, non-aqueous carriers or both and include, but are not limited to, aqueous suspensions, oil emulsions, water in oil emulsions, water-in-oil-in-water emulsions, site-specific emulsions, long-residence emulsions, sticky-emulsions, microemulsions, nanoemulsions and liposomes. Solid carriers are biological carriers, chemical carriers or both and include, but are not limited to, microparticles, nanoparticles, microspheres, nanospheres, minipumps, bacterial cell wall extracts and biodegradable or non-biodegradable natural or synthetic polymers that allow for sustained release of the MCC. Such polymers can be implanted in the vicinity of where delivery is required. Polymers and their use are described in, for example, Brem et al., J. Neurosurg. 74: 441–446 (1991).

Preferred aqueous carriers include, but are not limited to, DNase-free water, DNase-free saline and DNase-free physiologically acceptable buffers. Preferred non-aqueous carriers include, but are not limited to, mineral oil or neutral oil including, but not limited to, a diglyceride, a triglyceride, a phospholipid, a lipid, an oil and mixtures thereof, wherein the oil contains an appropriate mix of polyunsaturated and saturated fatty acids. Examples include, but are not limited to, soybean oil, canola oil, palm oil, olive oil and myglyol, wherein the number of fatty acid carbons is between 12 and 22 and wherein the fatty acids can be saturated or unsaturated. Optionally, charged lipid or phospholipid can be suspended in the neutral oil.

In an example, MCC is suspended in DNase-free sterile water and is sonicated at 20% output for 5 minutes (Model W-385 Sonicator, Heat Systems-Ultrasonics Inc). Optionally, the sonicated M-DNA is homogenized by microfluidization at 15,000–30,000 psi for one flow-through (Model M-110Y; Microfluidics, Newton, Mass.) and is transferred to an autoclaved, capped bottle for storage at 4° C. Optionally, MCC suspensions or M-DNA can be stabilized by the addition of non-ionic or ionic polymers such as polyoxyethylenesorbitan monooleate (Tween) or hyaluronic acid.

In an example, DNase free phosphatidylcholine is added to DNase free triglyceride soybean oil at a ratio of 1 gram of phospholipid to 20 ml of triglyceride and is dissolved by gentle heating at 50° C.–60° C. Several grams of MCC are added to a dry autoclaved container and the phospholipid-triglyceride solution is added at a concentration of 20 ml per 1 gram of MCC. The suspension is incubated at 20° C. for 60 min. and is then mixed with DNase-free PBS in the ratio of 20 ml MCC suspension per liter of DNase-free PBS. The mixture is sonicated at 20% output for 5 minutes (Model W-385 Sonicator, Heat Systems-Ultrasonics Inc.). Optionally, the sonicated MCC mixture is homogenized by microfluidization at 15,000–30,000 psi for one flow-through (Model M-110Y; Microfluidics) and is transferred to an autoclaved capped bottle for storage at 4° C.

The amount of MCC administered per dose, the number of doses and the dose schedule will depend on the type of inflammation, the severity of the inflammation, the location of the inflammation and other clinical factors such as the size, weight and physical condition of the recipient and the route of administration and can be determined by the medical practitioner using standard clinical techniques and without undue experimentation. In addition, in vitro assays may optionally be employed to help identify optimal range for MCC administration.

Preferably, the amount of MCC administered is from about 0.00001 to 100 mg/kg per dose, more preferably from about 0.0001 to 50 mg/kg per dose, and most preferably from about 0.001 to 20 mg/kg per dose. Preferably, the M-DNA content of the MCC is between about 0.001 and 90 mg/100 mg dry MCC, more preferably between about 0.01 and 40 mg/100 mg dry MCC, and most preferably between about 0.1 and 30 mg/100 mg dry MCC. Also, it is preferable that the protein content of the MCC be less than about 20 mg/100 mg dry MCC and the extractable M-DNA be at least about 4.5% of the dry weight of MCC.

Routes for administration include, but are not limited to, oral, topical, subcutaneous, transdermal, subdermal, intramuscular, intraperitoneal, intra-vesical, intra-articular, intra-arterial, intra-venous, intra-dermal, intra-cranial, intra-inflammation, intra-ocular, intrapulmonary, intra-spinal, placement within cavities of the body, nasal inhalation, pulmonary inhalation, impression into skin and electrocorporation. Depending on the route of administration, the volume per dose is preferably about 0.0001 ml to about 100 ml per dose, more preferably about 0.001 ml to about 60 ml per dose and most preferably about 0.01 ml to about 40 ml per dose.

The following examples will serve to further illustrate the present invention without, at the same time, however, constituting any limitation thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Preparation of MCC

MCC was prepared from *M. phlei* as described in International Patent Application No. PCT/CA98/00744, which is included by reference herein.

Briefly, to prepare MCC, *M. phlei* are grown in liquid medium and harvested. The *M. phlei* are disrupted, and the solid components of the disrupted *M. phlei* are collected by centrifugal sedimentation. The solid components are modified by deproteinization with DNase-free trypsin and DNase-free pronase, delipidation with DNase free urea and DNase-free phenol and washing with DNase-free water.

All reagents used in the preparation of MCC were selected to enhance conservation of the DNA. Unless stated otherwise, MCC was resuspended in DNase-free water or in a pharmaceutically acceptable DNase-free buffer and emulsified by sonication. MCC did not contain endotoxins as determined using a Limulus amebocyte lysate QCL-1000 kit (BioWhittaker, Walkersville, Md.).

EXAMPLE 2
Preparation of BCC from Mycobacterial Species other than *M. phlei*

BCC is prepared from mycobacterial species including, but not limited to, *M. vaccae, M. chelonei, M. smegmatis, M. terrae, M. duvalii, M. tubeculosis, M. bovis* BCG, *M. avium, M. Szulgai, M. scrofulaceum, M. xenopi, M. kansaii, M. gastr, M. fortuitous* and *M. asiaticum* as in Example 1.

EXAMPLE 3
Administration of MCC and Induction of Inflammation 6.7 mg kg$^{-1}$ MCC in saline (experimental) or saline (control) were administered to female CD-1 mice (Charles River, Saint Constant, Quebec, Canada) intravenously in 0.2 ml; intraperitoneally in 1.0 ml; subcutaneously, into the hind footpad, in 0.05 ml; and, orally, using a feeding needle, in 0.2 ml. Two h later a 1% solution of carrageenan (Sigma-Aldrich, Mississauga, Ontario, Canada) in a final volume of 0.05 ml was injected into the hind footpad of each mouse to induce inflammation. Footpad swelling was quantified by measuring water-displacement at 0, 3, 24, 48, 72 and 96 h after carrageenan injection (Filion et al. British Journal of Pharmacology 122:551–557, 1997).

EXAMPLE 4
Anti-Inflammatory Effect of MCC

Carrageenan induced inflammation was detected at 3 h, peaked at 48 h and began to decrease at 72 h. Both intravenous and oral administration of MCC produced a significant reduction in footpad inflammation (volume) within 3 h after carrageenan injection. Maximum reduction of inflammation occurred at 48 h after both intravenous (58% reduction) and oral (57% reduction) administration of MCC and persisted for at least 72 h (FIG. 1 & FIG. 2).

Subcutaneous administration of MCC into the hind footpad, 2 h before carrageenan injection into the same hind footpad, also reduced inflammation. However, this was not evident until 24 h after carrageenan injection. Maximum reduction in inflammation was 40% and occurred at 48 h (FIG. 1 & FIG. 2).

Figure 2:
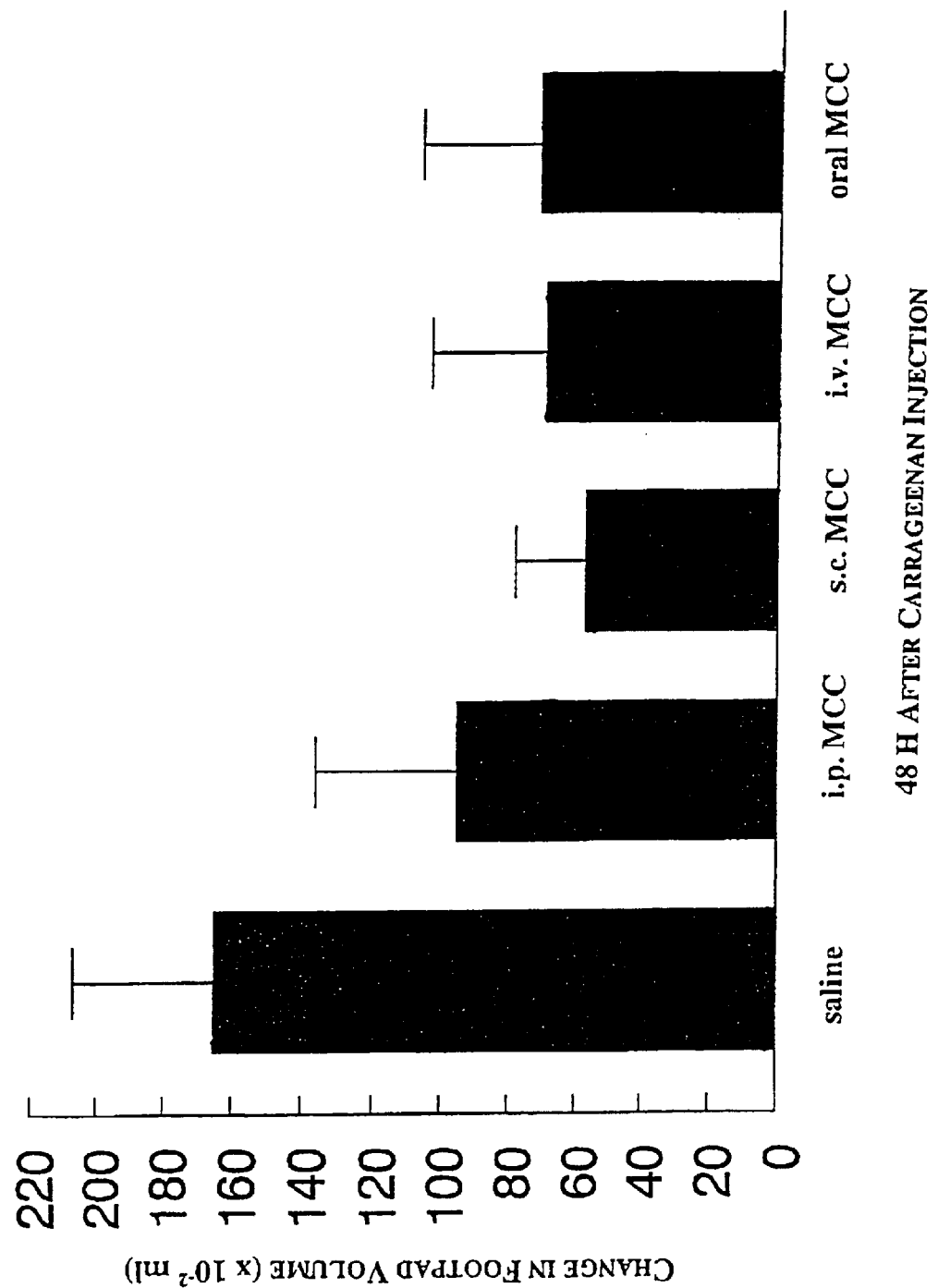
FIG. 2. Effect of intravenous, intraperitoneal, oral and subcutaneous MCC on mouse footpad volume at 48 h after carrageenan injection. Results are the mean±SD (vertical line) for 8 mice per group.

Intraperitoneal administration of MCC provided minimal reduction in inflammation for 48 h and, by 72 h, there was no difference in footpad volume between experimental and control mice (FIG. 1 & FIG. 2).

EXAMPLE 5
IL-10 Induction by MCC

The ability of MCC to induce IL-10 and TNF-alpha synthesis was evaluated. IL-10 is an anti-inflammatory cytokine (Isomake et al. Annals of Medicine 29:499–507, 1997). TNF-alpha is a pro-inflammatory cytokine (Shanley et al. Molecular Medicine Today 1:40–45 1995).

Groups of four mice each received 6.7 mg kg$^{-1}$ MCC in 0.2 ml of saline intravenously (experimental), 6.7 mg kg$^{-1}$ or 50 mg kg$^{-1}$ MCC in 1.0 ml of saline intraperitoneally (experimental), 6.7 mg kg$^{-1}$ MCC in 0.2 ml of saline orally (experimental) or saline (control). Blood was obtained from the tail vein of the mice and IL-10 and TNF-alpha in the serum were quantified at 0, 3, 6 and/or 24 h after MCC administration using the appropriate ELISA kit (BioSource, Camarillo, Calif.).

Figure 3:
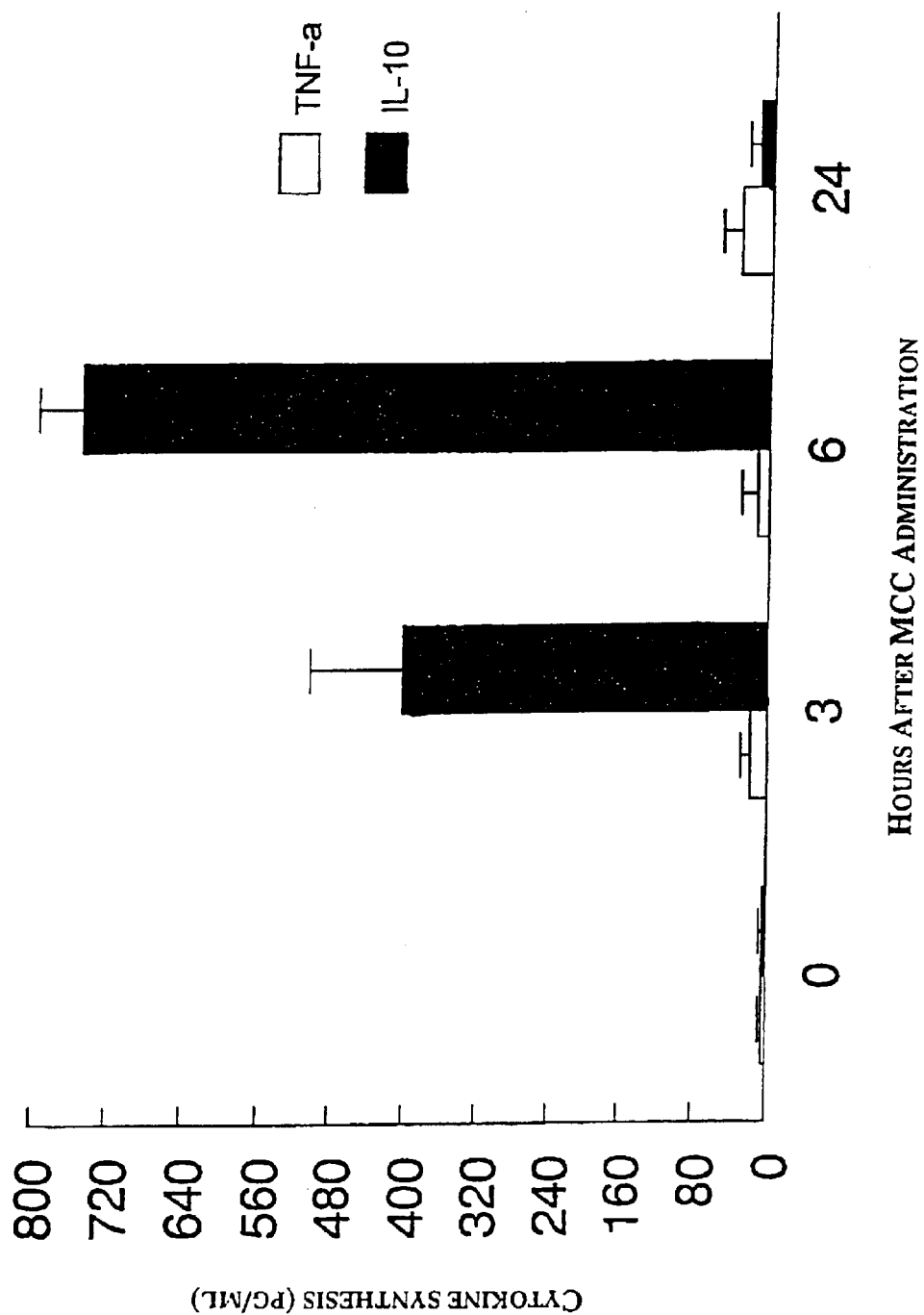
FIG. 3. Effect of intraperitoneal MCC on TNF-alpha and IL-10 synthesis at 0, 3, 6 and 24 h after administration. Results are the mean ±SD (vertical line) for 4 mice per group.
Figure 4:
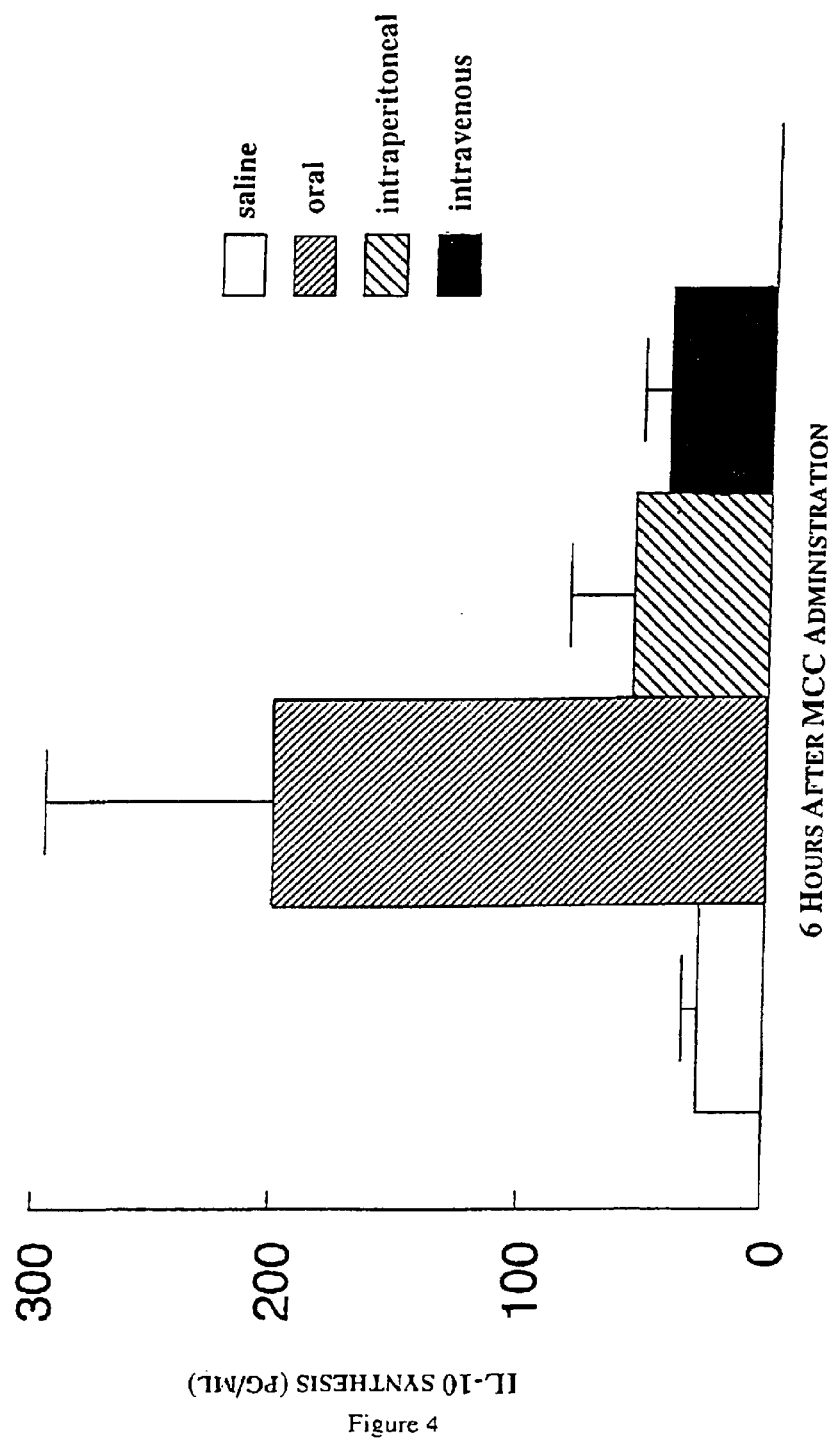
FIG. 4. Effect of intraperitoneal, intravenous and oral MCC on IL-10 synthesis at 6 h after administration. Results are the mean ±SD (vertical line) for 4 mice per group.

Mice administered 50 mg kg$^{-1}$ MCC intraperitoneally showed a significant increase in the anti-inflammatory cytokine IL-10, which peaked at 6 h, and showed no significant increase in the pro-inflammatory cytokine TNF-alpha (FIG. 3). Mice administered 6.7 mg kg$^{-1}$ MCC either intraperitoneally or intravenously showed a minimal increase in IL-10 synthesis at 6 h, whereas mice administered 6.7 mg kg$^{-1}$ MCC orally showed a significant increase in IL-10 synthesis at 6 h (FIG. 4).

EXAMPLE 6
MCC Treatment of Osteoarthritis

Ten patients with debilitating osteoarthritis were administered MCC intravenously twice per week for four weeks. Eight of the ten patients reported a significant reduction in pain and a significant increase in their ability to perform routine tasks.

EXAMPLE 7
MCC Treatment of Colitis

Fifteen patients with colitis were divided into three groups. Once each day for sixty days Group 1 patients received saline orally, Group 2 patients received cortisone orally and Group 3 patients receive MCC orally. At the end of the thirty days, Group 1 patients reported no reduction in symptoms. Group 2 patients reported a reduction in colitis symptoms, but complain of cortisone side effects. Group 3 patients reported a reduction in colitis symptoms without any mention of side effects.

It should be understood, of course, that the foregoing relates only to preferred embodiments of the present invention and that numerous modifications or alterations may be made therein without departing from the spirit and the scope of the invention as set forth in the appended claims.

We claim:

1. A method for reducing inflammation in an animal having inflammation, comprising administering to the animal an effective amount of a composition comprising:
   (a) a mycobacterial deoxyribonucleic acid obtained from a disrupted mycobacterium, wherein the mycobacterial deoxyribonucleic acid is preserved and complexed on a mycobacterial cell wall (BCC); and
   (b) a pharmaceutically acceptable carrier, wherein the amount is effective to treat the inflammation.

2. The method of claim 1, wherein the effective amount is effective to induce the synthesis of cytokine IL-10.

3. The method of claim 1, wherein the pharmaceutically acceptable carrier is selected from the group consisting of a liquid carrier and a solid carrier.

4. A method for reducing inflammation in an animal having inflammation, comprising administering to the animal an effective amount of a composition comprising *Mycobacterium phlei*-DNA preserved and complexed on a *Mycobacterium phlei* cell wall (MCC) and a pharmaceutically acceptable carrier, wherein the amount is effective to reduce the inflammation.

5. The method of claim 4, wherein the effective amount is effective to induce the synthesis of cytokine IL-10.

6. The method of claim 4, wherein the pharmaceutically acceptable carrier is selected from the group consisting of a liquid carrier and a solid carrier.

7. The method of claim 1, wherein the mycobacterial deoxyribonucleic acid and the mycobacterial cell wall are obtained from *Mycobacterium phlei*.

8. The method of claim 1, wherein the animal has immune-mediated inflammation, osteoarthritis, rheumatoid arthritis, glomerulonephritis, colitis or cystitis.

9. The method of claim 1, wherein the animal has osteoarthritis.

10. The method of claim 1, wherein the animal has colitis.

11. The method of claim 1, wherein the *Mycobacterium* is selected from the group consisting of *M. vaccae, M. chelonei, M. smegmatis, M. terrae, M. duvalii, M. tuberculosis, M. bovis* BCG, *M. avium, M. Szulgai, M. scrofulaceum, M. xenopi, M. kansaii, M. gastr, M. fortuitious*, or *M. asiaticum*.

12. The method of claim 4, wherein the animal has immune-mediated inflammation, osteoarthritis, rheumatoid arthritis, glomerulonephritis, colitis, or cystitis.

13. The method of claim 4, wherein the animal has osteoarthritis.

14. The method of claim 4, wherein the animal has colitis.

15. A method for inducing IL-10 production in an animal comprising administering to the animal an effective amount of a composition comprising:
   (a) a mycobacterial deoxyribonucleic acid obtained from a disrupted *Mycobacterium*, the mycobacterial deoxyribonucleic acid preserved and complexed on a mycobacterial cell wall (BCC); and
   (b) a pharmaceutically acceptable carrier, wherein the amount is effective to induce IL-10 production.

16. The method of claim 15, wherein the pharmaceutically acceptable carrier is selected from the group consisting of a liquid carrier and a solid carrier.

17. The method of claim 15, wherein the mycobacterial deoxyribonucleic acid and the mycobacterial cell wall are obtained from *Mycobacierium phlei*.

18. The method of claim 15, wherein the *Mycobacterium* is selected from the group consisting of *M. vaccae, M. chelonei, M. smegmatis, M. terrae, M. duvalii, M. tuberculosis, M. bovis* BCG, *M. avium, M. Szulgai, M. scrofulaceum, M. xenopi, M. kansaii, M. gastr, M. fortuitious*, or *M. asiaticum*.

19. A method for inducing IL-10 production in an animal, comprising administering to the animal an effective amount of a composition comprising *Mycobacterium phlei*-DNA preserved and complexed on a *Mycobacterium phlei* cell wall (MCC) and a pharmaceutically acceptable carrier, wherein the amount is effective to induce IL-10 production.

20. The method of claim 19, wherein the pharmaceutically acceptable carrier is selected from the group consisting of a liquid carrier and a solid carrier.

21. The method of claim 19, wherein the animal has immune-mediated inflammation, osteoarthritis, rheumatoid arthritis, glomerulonephritis, colitis, and cystitis.

* * * * *